United States Patent
Kruger et al.

[11] Patent Number: 5,890,897
[45] Date of Patent: Apr. 6, 1999

[54] ADJUSTABLE LENGTH DRILLS

[76] Inventors: Bernard M. Kruger, 5 Natalie Dr., West Caldwell, N.J. 07006; Charles J. Stipo, 37 DeGroat Rd., Wantage Township, Sussex, N.J. 07461

[21] Appl. No.: 685,920

[22] Filed: Jul. 22, 1996

[51] Int. Cl.⁶ .............. A61C 3/02; B23B 51/00
[52] U.S. Cl. ................ 433/75; 433/165; 606/172; 408/202
[58] Field of Search .............. 433/72, 75, 102, 433/165; 408/192, 202, 241 S; 606/80, 172; 604/117

[56] References Cited

U.S. PATENT DOCUMENTS

| | | |
|---|---|---|
| 412,952 | 10/1889 | Elterich . |
| 2,344,143 | 3/1944 | Harding . |
| 3,301,101 | 1/1967 | McEwen . |
| 3,576,076 | 4/1971 | Weissman .................. 433/165 |
| 3,855,705 | 12/1974 | Malmin ........................ 433/72 |
| 4,039,266 | 8/1977 | O'Connell .................... 408/202 |
| 4,076,443 | 2/1978 | Halpern . |
| 4,710,075 | 12/1987 | Davison ...................... 408/202 |
| 4,978,261 | 12/1990 | Wright, III ................. 408/241 S |
| 5,261,818 | 11/1993 | Shaw .......................... 433/165 |
| 5,382,120 | 1/1995 | Parsons ....................... 408/202 |
| 5,569,035 | 10/1996 | Balfour et al. ................ 433/165 |

FOREIGN PATENT DOCUMENTS

| | | | |
|---|---|---|---|
| 668698 | 1/1989 | Switzerland .................. 433/72 |
| 501331 | 8/1938 | United Kingdom ........... 408/241 S |

*Primary Examiner*—Ralph A. Lewis
*Attorney, Agent, or Firm*—Ralph T. Lilore

[57] ABSTRACT

A drill instrument with calibrated depressions as markings on the shaft set at determinable distances apart, e.g. at 1 mm increments is disclosed. These calibrations are designed to give a visible depth gauge indication when the tip or point of the drill is at the full length of the depth of a drilled hole. A stop means is variably fixable to the drill at determinable locations. This stop defines a predetermined length available for drilling a hole into bone or a tooth canal up to the precise location of the stop on the drill corresponding to the depth desired to be drilled.

An organizer block or kit accommodates the drills and stops of the invention and preferably provides an alignment device for preparing drills having the pre-determined lengths according to the invention via a drill-length determining device for applying the stop means to the drill at the desired pre-determined length.

19 Claims, 3 Drawing Sheets

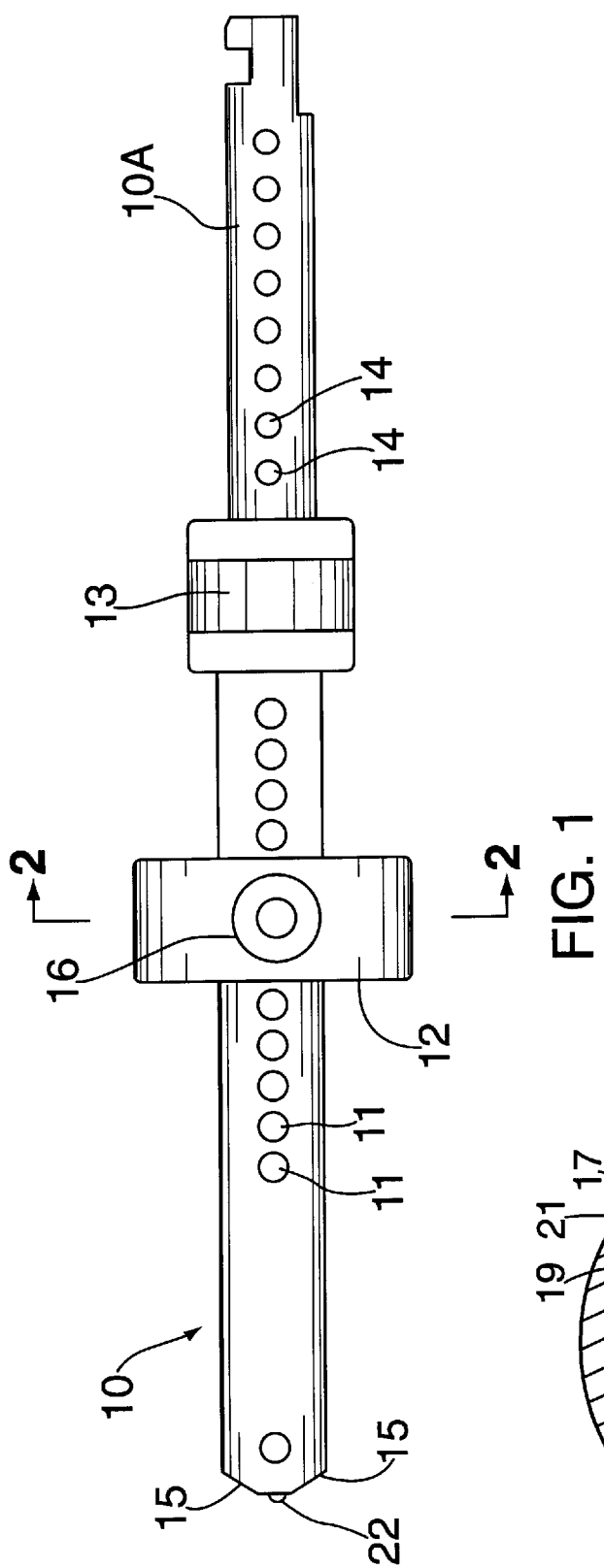
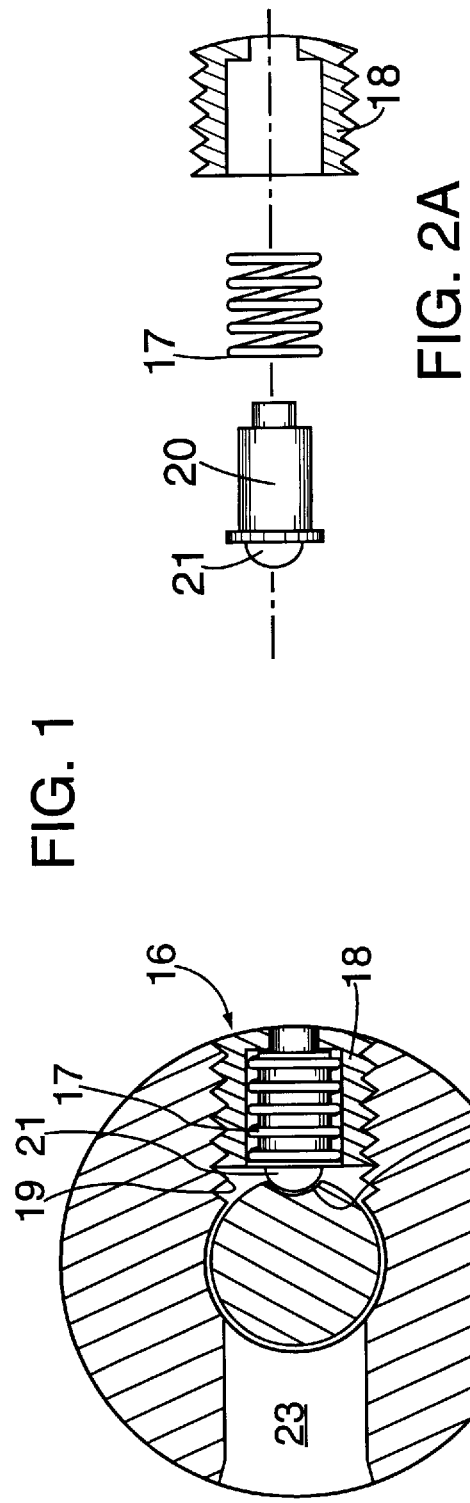

ADJUSTABLE LENGTH DRILLS

This invention relates to drill-cutting devices in general and more particularly to drills having adjustable drilling lengths. It further relates to drills which are equipped with an adjustable collar or stop which can be used to alter the cutting length of the drill and, therefore, the depth to which the drill will cut. Still more specifically, it relates in specific embodiments to drills used in dental procedures.

BACKGROUND OF THE INVENTION

There are many procedures encountered where the drilling of holes to specified depths is required. This is especially true in dental procedures. For example, when a dentist is involved in a procedure in which a hole or channel must be drilled in bone or in the canal of a root, several major hurdles and obstacles are encountered. Since the depth of the hole to be drilled is not visible to the naked eye as drilling proceeds, ancillary diagnostic equipment must be used to give an indication as to when the proper depth has been reached. This, in some cases, involves using x-rays to locate a probe in the canal or the hole in the bone. In some cases it involves the use of an electronic device in which the patient is grounded and a circuit completed between the patient and the metal instrument which is inserted into the canal.

The problem is especially acute in dealing with drilling into bone in dental implant procedures. In these cases, it is extremely important that a precisely constructed depth of drilling be obtained because the internal structures in the jawbones are filled with areas that could be seriously damaged were they to be struck with the drill. Such structures as nerves, muscles, and sinuses are especially vulnerable because the dentist cannot see these structures as drilling proceeds.

In practice, once the length of the canal or the location of sensitive structure is accurately determined, the dentist is then faced with the problem of fixing that length in a manner in which the depth can be accurately measured. Current techniques for performing this depth measurement as, for example, by holding the canal probe with forceps at the level at which it exits the canal, removing the probe and measuring the distance between the tip of the probe and the forceps, are cumbersome. The dentist can only estimate when the appropriate drilling depth has been reached. This technique gives rise to error and is fraught with the possibility of mishandling.

For determining the location of critical structures, measurements must be taken from x-rays and transferred to the drilling instrument. Yet there is no reliable way to transfer these measurements to the drill and maintain the same during drilling. The dental profession is constantly seeking new and alternative means for fixing the drilling depth of a drill in a simple way so that when drills of different lengths and diameter are used to drill a hole in bone or in a canal, the dentist will know that the appropriate depth has been obtained when a predetermined part of the drill has been reached.

SUMMARY OF THE INVENTION

Accordingly, the invention presented herein is intended to alleviate some of the problems presented by the prior art and to provide a more simple approach to drilling a hole to a predetermined depth. In the description of the invention herein, reference will be made to the following figures:

FIG. 1 is a drill instrument with calibrated depressions as markings on the shaft set at determinable distances apart, e.g. at 1 mm increments. These calibrations are designed to give visible depth gauge indication when the tip or point of the drill is at the full length of the depth of the canal or hole in bone, for example.

FIG. 2 is a cross-section along A—A of FIG. 1 and shows one aspect of the devices of the present invention in which a stop means is applied to the drill at determinable locations. This stop defines a predetermined length available for drilling a hole or into a canal up to the precise location of the stop on the drill corresponding to the depth desired to be drilled.

FIG. 2a is an embodiment of one element of the stop shown in FIG. 2.

Figure 3:
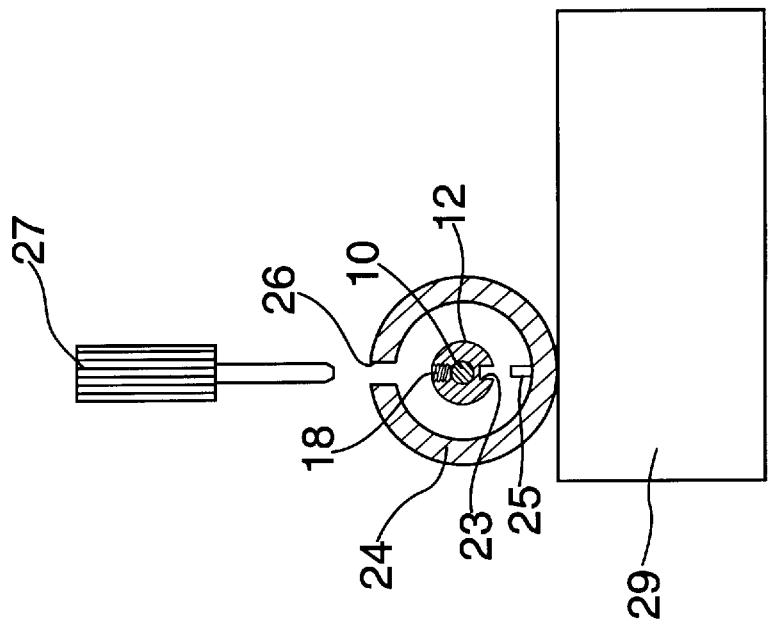
Figure 4:
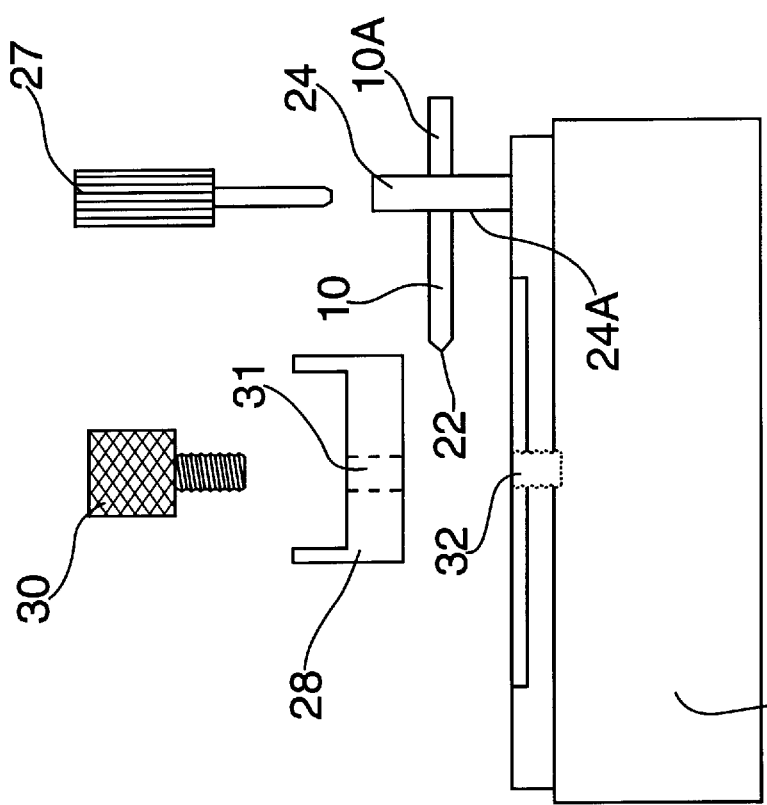
Figure 5:
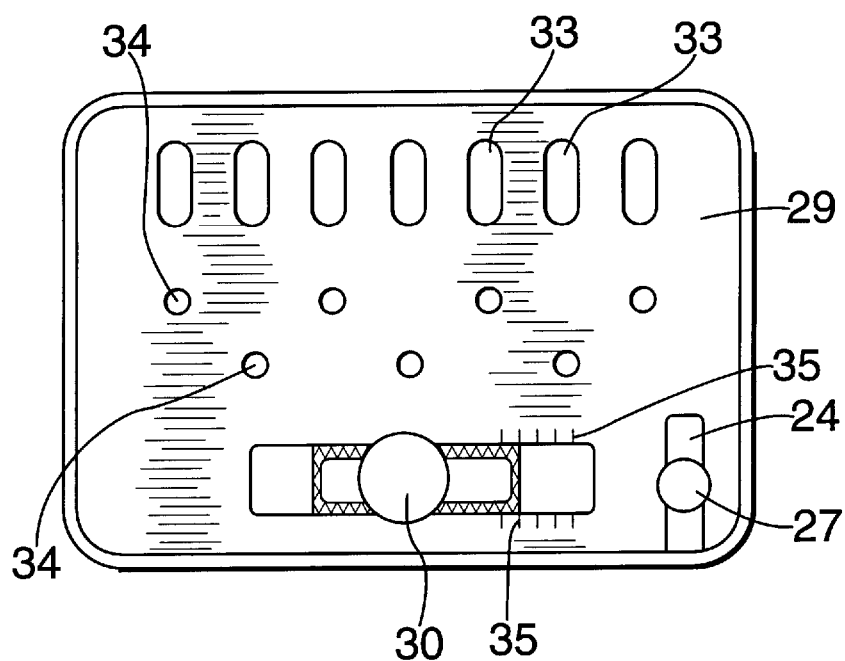

FIGS. 3, 4, and 5 are composites showing elements of the invention in a kit which may be used to achieve drilling to predetermined depths wherein FIG. 3 shows an alignment device present on an organizer block shown on FIG. 5, FIG. 4 shows an exploded view of the elements of FIG. 5, and FIG. 5 is a representation of the organizer block or kit which accommodates the drills and stops of the invention, the alignment device for preparing drills having pre-determined lengths according to the invention and the drill-length determining device shown in FIG. 4 for applying the stop means to the drill at the desired pre-determined length.

DETAILED DESCRIPTION OF THE INVENTION

In dental practice, the dentist is often called upon to conduct procedures which require an awareness of the length of a canal or hole to be drilled in tooth or bone so that the depth to which a drill should be inserted may be precisely known. This is particularly true when conducting a root canal procedure or in drilling a hole into bone for anchoring implants. In a root canal procedure, the dentist uses files and reamers of gradually increasing diameter to sequentially open the canal and file it into a uniform tapered shape. This will facilitate the insertion of a sufficient amount of properly located canal filling material. By "properly located" is meant the essentially complete filling of the canal to its apex. Failure to do so could lead to complications of infection, pain, and perhaps ultimate loss of the tooth. In drilling holes for insertion of anchoring pins for implant prostheses, knowledge of the location of critical structures is important so that damage to these structures does not occur because of uncontrollable drilling to what should be precisely located end points.

The present invention encompasses three aspects which are generally used together to achieve the objects described above. The first is a drill which is capable of receiving stop means at intervals sufficient to provide measurements of distance from the drilling point of the drill. Preferably, the shaft is calibrated, most preferably at 1 mm intervals, by the placement of depressions thereon, the depressions cooperating with the stop means to anchor the stop means to the shaft. The calibrated drill is thus used in conjunction with the stop means variably fixable on the drill with fastening means. The stop is generally made of the same material as the drill, i.e. high quality medical grade stainless steel, although if non-medical applications are desired, then any appropriate material may be used. The stop is preferably cylindrical and collar-like in shape and has a hole transversely located to facilitate application around the shaft. Within the stop is a hole at an appropriate location to receive fastening means, such as a spring or screw meant to engage the second, preferred, aspect of the invention, i.e. a means such as a depression on the drill, which receives the fastening means of the stop thereby to provide between the drill point and the nearest stop surface, a precise length to which the drill will be used. The stop shown in FIG. 2 represents a unitary mechanism whereby a spring element can be opened or disengaged from the depressions to accommodate drilling lengths by the expedient of a screw or other means for engaging and disengaging the spring. Instead of a spring, the screw itself may be used to its full length to engage the depressions, but this is not preferred.

In use, the dentist, desiring to determine the length of the canal or hole to be drilled, utilizes art-known techniques for determining said length, preferably by x-ray, cat-scan, magnetic resonance imaging or the like. The stop is then applied to the drill to engage the means or depression at the position which will locate the stopping surface at a point corresponding to the desired length of the drill. If the depressions are calibrated, one need only count the calibrations to set the stop at the appropriate length. If the shaft is not otherwise calibrated, the invention also provides a means by which the stop means can be properly and accurately placed as described in relation to FIG. 5. From that point on, all instruments or drills subsequently used will have the stop placed at exactly that location so that the dentist will always know that a drill or instrument of the desired length is being used.

In summary, the present invention comprises a device such as a drill or instrument having means, preferably depressions, and most preferably calibrated depressions, placed on the shaft thereof, at determinable distances from the end point of the device, stop means positionable on said device comprising means for securing said stop means to said device at a desired length of said device wherein said means include an element engageable with said calibration means in locking fashion and disengageable therefrom. A third aspect of the invention is the provision of an organizer block which facilitates not only storage and shipping of components, but also placement of the stop to the drill at the precise location needed for drilling to the desired depth.

The invention will be more fully understood when the accompanying drawings are considered. Reference to FIG. 1 illustrates a particular embodiment of the invention wherein a drill 10 is provided. Placed at determinable lengths and distances along the drill are depressions 11 which can be used to engage a fastening means 16 on stop 12. The drill shaft includes a ridge 10B running vertically on the drilling portion adjacent to the depressions 11 which is capable of engaging the fastening means 16 when the fastening means is disengaged from the depressions 11 in order to restrict the free rotation of the drill shaft in the stop member 12. The manner in which stop 12 engages the drill via fastening means 16 is shown more clearly in FIG. 2 as a combination of screw 18 (see also FIG. 2A) turned into the tapped hole 19 of the stop 12, compressing spring 17 against engagement pin 20 which communicates via engagement head 21 with depression 11 on the shaft of the drill 10. Fastening means 16 can be brought to bear upon depression 11 by turning the screw 18 into the tap hole. Spring 17 fitted with an engagement pin 20 having an engagement head 21 is engageable with depression 11 such that when the screw is advanced into the stop 12, the spring becomes depressed against the depression 11 at the desired location and the engagement pin 20 locks into the shaft. Also provided in stop 12 is an anchoring hole 23 which is provided in a preferred embodiment to assist in fastening stop 12 to shaft 10 through the use of a fastening device shown in FIG. 3 which may or may not be part of the organizer block shown in FIG. 4.

The FIG. 2 representation is a cross-section of the stop 12 taken at line A—A shown in FIG. 1. Connector 13 is a connection shown for purposes of illustration only, which connects to a shaft 10A insertable into a drill bit of the motor for the drill. In addition, as a preferred embodiment, shaft 10A is provided with elements 14 shown on the shaft which can be in the form of painted areas or other discernible elements on the shaft such as a raised pimple or a depression. These elements are used to indicate the number of times a drill has been used. For example, if 14 were painted dots, then each time the drill is used, one of the painted dots would be burnished off showing the number remaining for the useful life of a drill. In this regard, many drills, even of the best medical grade materials, can only be used from 8–12 times. It should be noted that shafts 10 and 10A may be one continuous piece, the 10A portion of which is insertable into the drill turning device.

The preferred embodiment shown in FIG. 2 wherein the spring means is the means by which the engagement of the depression 11 is facilitated is merely a preferred means of so engaging. Alternatively, other forms of engagement and locking can be used. For example, the tapped hole 19 in the stop 12 can be made narrower than the depression 11 and the screw itself advanced to reside within the depression. Alternatively, another embodiment would be to use the screw shown in FIG. 2a, but instead of a spring attachment 17 within the screw 18 there could be a protrusion which, upon advancement of the screw, would engage depression 11. A variety of engaging systems can be used at this point.

Reference is now made to FIG. 3 wherein a stop-affixing device 24 is provided to aid in placing the collar at the appropriate length of the drill 10. In use, stop 12 is placed over alignment post 25 such that anchoring hole 23 is in alignment therewith and screw 18 is aligned vertically. Screwdriver 27 is provided to pass through opening 26 to engage screw 18 to tighten against shaft 10 protruding out of the plane of the paper. The remaining part of shaft 10 is shown in exploded view FIG. 4 which shows a depth alignment device for affixing the stop 12 at the appropriate dimension. This is achieved by having carriage 28 slidably mountable on organizer block 29 and securable thereto via screw 30 insertable through opening 31 into tapped opening 32. The distance between the edge of carriage 28, abutting tip 22, and the nearest edge 24A of stop-affixing device 24 is of variable dimensions and, as shown in FIG. 5, can have dimension lines 35 placed thereon to move throughout the range of desired lengths. Referring again to FIG. 3, shaft 10 can be moved horizontally through its collar with screw 18 loosened until the desired length is obtained and then carriage 28 may be anchored via screw 30 to organizer block 29. Screw 18 in stop 12 can then be tightened to thereby affix stop 12 to shaft 10. Openings 33 in organizer block 29 (see FIG. 5) can be used to accommodate differing stop diameters whereas openings 34 are provided to store shafts 10 of differing diameters.

In use, when it is desired to drill a hole into bone, the dentist often uses as a first drill a taper which is used to align the channel in the bone. Accurate depth measurements are not ordinarily required at this point except that the dentist would wish to remain short of the desired length. The cutting surfaces of the taper are usually such that there is cutting by the end of the taper as well as by the sides of the taper.

After the channel is aligned, the dentist then would use a drill which has only end-cutting surfaces and which is used to obtain the proper depth. Drills of approximately 1.6 mm in diameter are normally employed. Having used the depth-defining drill, the dentist thereafter seeks to widen the channel gradually through the sequential use of drills having larger and larger diameters up to the ultimate diameter desired in the channel. Such drills generally have a cutting edge shown as a heavier black line 15 in FIG. 1 which does not traverse the entire length of the advancing edge. The purpose is to provide an end-cutting surface sufficient in length merely to cut the incremental bone met by the drill necessary to be removed for widening. It is desirable that the only cutting that occurs is in the widening direction and not in a depth direction. In the normal course of events in practicing the invention, the depth is controlled by the presence of the collar affixed at the appropriate length. As a safety feature, however, should there be a malfunction of stop 12, there is provided a half-round tip 22 which meets the end of the channel at the desired length providing a separation between cutting edges 15 and the bone at the bottom of the hole so that drill 10 cannot be advanced beyond the pre-established depth dimension of the channel. This prevents drill 10 from going any further if stop 12 comes loose.

As a further embodiment of the invention, drill 10 has an internal channel running longitudinally to provide a flow of water for cooling purposes.

We claim:

1. A drill of variable length comprising
   a) a generally cylindrically shaped drill shaft having a drilling portion which terminates in a drilling end point, the surface of said end point comprising an end-cutting surface and a plurality of recesses arranged vertically on said drilling portion at various distances from said end point,
   b) a stop member having an outer perimeter and a bore therethrough said bore constituting an inner perimeter to permit the slidable positioning of said stop member around said drilling portion, said inner perimeter and said outer perimeter constituting an interface,
      i) said stop member including a first hole extending from the outer perimeter thereof through said stop member and terminating at said interface, such that said first hole is registerable with at least one of said recesses,
      ii) said first hole having screw fastening means for locking engagement and disengagement with at least one of said recesses at said interface thereby to fasten said stop member to said drilling portion when said screw fastening means engages said recess and to unfasten said stop member when said screw fastening means is disengaged from said recess,
      iii) said stop member further including an anchoring hole in said outer perimeter essentially opposite said first hole, said anchoring hole being engageable with a fixed alignment device whereby when said stop member engages said fixed alignment device the slidable movement of said drilling portion through said stop member is facilitated.

2. The drill of claim 1 wherein said recesses are depressions in the drilling portion of said drill.

3. The drill of claim 2 wherein said depressions are located at predetermined distances from said end point.

4. The drill of claim 3 wherein said stop member is in the form of a cylindrical collar having screw threads in said first hole, and said screw fastening means include screw means for locking engagement and disengagement with said depressions.

5. The drill of claim 4 wherein the lockingly engageable means is spring biased.

6. The drill of claim 4 wherein the lockingly engageable means is a screw directly engageable with said depressions.

7. The drill of claim 6 wherein said drilling end point comprises a cutting edge which does not traverse the entire length of the advancing edge, thereby providing an end-cutting surface sufficient to cut incremental bone only in a widening direction and not substantially in a depth direction.

8. The drill of claim 6 wherein the non-drilling portion includes markings thereon which may be altered after each use of said drill thereby indicating the number of times a drill has been used.

9. A kit comprising a plurality of drills of claim 1 and a drill length setting device comprising a housing block, a moveable abutting edge slidably mounted at determinable calibrated markings on said block and adapted to abut the end point of said drills onto which a stop member is slidably positioned, and an alignment device capable of holding said stop member while positioned on said drill in a fixed, determinable position on said drill, means for fastening said stop member on said drill at a distance from said end point which corresponds to the desired length of said drill, said length being defined by said abutting edge and said stop member.

10. The kit of claim 9 comprising said drills in various drill diameters.

11. The kit of claim 9 wherein the alignment device is an alignment post.

12. The drill of claim 1 wherein the screw fastening means is a ball, spring, and screw locking structure.

13. The drill of claim 1 wherein said drill shaft includes a ridge running vertically on said drilling portion adjacent to said plurality of recesses capable of engaging said screw fastening means when said screw fastening means is disengaged from said recess thereby to restrict the free rotation of said drill shaft in said stop member.

14. The drill of claim 13 wherein said recesses are depressions in the drilling portion of said drill.

15. The drill of claim 14 wherein said depressions are located at predetermined distances from said end point.

16. The drill of claim 15 wherein the lockingly engageable means is a screw directly engageable with said depressions.

17. The drill of claim 16 wherein said drilling end point comprises a cutting edge which does not traverse the entire length of the advancing edge, thereby providing an end-cutting surface sufficient to cut incremental bone only in a widening direction and not substantially in a depth direction.

18. The drill of claim 17 wherein the non-drilling portion includes markings thereon which may be altered after each use of said drill thereby indicating the number of times a drill has been used.

19. The drill of claim 18 wherein said drilling end point is provided with a tip positioned to meet the end of a drilled channel thereby providing a separation from said end and said end cutting surface.

* * * * *